United States Patent [19]

Rudolph et al.

[11] 4,382,897

[45] May 10, 1983

[54] PROCESS FOR THE PREPARATION OF TRIFLUORACETIC ACID DERIVATIVES

[75] Inventors: Werner Rudolph; Guenter Fernschild, both of Hanover, Fed. Rep. of Germany

[73] Assignee: Kali Chemie AG, Hanover, Fed. Rep. of Germany

[21] Appl. No.: 287,730

[22] PCT Filed: Nov. 21, 1980

[86] PCT No.: PCT/EP80/00134

§ 371 Date: Jul. 23, 1981

§ 102(e) Date: Jul. 23, 1981

[87] PCT Pub. No.: WO81/01406

PCT Pub. Date: May 28, 1981

[51] Int. Cl.$^3$ ............................................. C07C 51/58
[52] U.S. Cl. ................................................. 260/544 Y
[58] Field of Search ...................... 260/544 Y; 562/541

[56] References Cited

U.S. PATENT DOCUMENTS

| | | | |
|---|---|---|---|
| 2,396,076 | 3/1946 | Benning et al. | 562/541 |
| 3,051,749 | 8/1962 | Lawlor et al. | 562/541 |
| 3,102,139 | 8/1963 | Lawlor et al. | 260/544 Y |
| 3,151,051 | 9/1964 | Braid et al. | 204/158 |
| 3,160,659 | 12/1964 | Dittman et al. | 260/544 Y |
| 3,725,475 | 4/1973 | Paucksch et al. | 260/544 Y |

*Primary Examiner*—Natalie Trousof
*Assistant Examiner*—L. Hendriksen
*Attorney, Agent, or Firm*—Schwartz, Jeffery, Schwaab, Mack, Blumenthal & Koch

[57] ABSTRACT

Good yields of trifluoracetyl compounds, particularly trifluoracetyl chloride, are obtained with short reaction times by the reaction of 1,1,1-trifluoro-2,2,2-trichloroethane with sulfur trioxide in the presence of mercury salts and additionally boron halides and/or halosulfonic acid.

16 Claims, No Drawings

4,382,897

PROCESS FOR THE PREPARATION OF TRIFLUORACETIC ACID DERIVATIVES

BACKGROUND OF THE INVENTION

The invention concerns a process for the preparation of trifluoroacetyl compounds, in particular trifluoracetyl chloride by the reaction of 1,1,1-trifluoro-2,2,2-trichloroethane with sulfur trioxide in the presence of mercury salts.

Such a process is known from U.S. Pat. No. 3,160,659. According to this reference, perfluoroacetyl chloride may be obtained by introducing fuming sulfuric acid or SO$_3$, slowly into trifluorotrichlorethane, to which mercury sulfates have been added as catalysts, at the reflux temperature and subsequently maintaining the mixture at the boiling temperature for a longer period of time. After a few hours, the trifluoracetyl chloride begins to distill off. Several days are needed to complete the reaction.

The preparation of fluorine containing perhalogen carboxylic acids by solvolysis is also difficult. The solvolysis of perchlorinated aliphatic compounds containing one or more CCl$_3$ groups is relatively simple. They may be converted by means of a moderately concentrated sulfuric acid to carboxylic acids having one or more carboxyl groups, such as described, for example, by H. Henecka in Houben, Weyl, "Methods of Organic Chemistry", Vol. 8, p. 427. If one or several fluorine atoms are present adjacently to the terminal CCl$_3$ group, carboxylic acid is formed only when sulfuric acid containing free SO$_3$ or SO$_3$ are added. By varying the SO$_3$ content of the sulfuric acid, the ratio of the amount of SO$_3$ to the alkane halide, the reaction temperature or the reaction time, attempts were made to improve the process so that industrial applications would be possible. The conversion is effected in part in the absence and in part in the presence of catalysts, such as mercury sulfates (U.S. Pat. Nos. 2,396,076 and 3,102,139). However, the reaction rates of the processes, which may be only be carried out discontinuously, remain unsatisfactory. A further disadvantage of these processes is the frequently laborious recovery of the acid from the reaction mixture. The latter generally is diluted with water and the acid recovered by means of extensive and costly extraction processes. The acid often decomposes during processing, which again reduces the yield.

According to German Pat. No. 19 17 630, fluorine-containing perhalogenated carboxylic acid fluorides or chlorides are prepared from fluorochloroalkanes by reaction with SO$_3$ in the presence of catalytic amounts of mercury sulfates. This process is suitable for continuous operation, wherein usable but not optimum space-time yields are obtained.

SUMMARY OF THE INVENTION

The invention is based on the object of overcoming the disadvantages of the state of the art. Surprisingly, the reaction may be accelerated, particularly in a discontinuous operation, by reacting 1,1,1-trifluoro-2,2,2-trichloroethane with sulfur trioxide in the presence of mercury salts, wherein the reaction is effected according to the invention additionally in the presence of the boron halide BX$_3$ (X=F, Cl, Br, I) and/or halosulfonic acid HSO$_3$Y (Y=F, Cl, Br, I). Both for X and for Y, chlorine or bromine are the preferred halogen.

A variant of the process according to the invention involves carrying out the reaction in the presence additionally of only boron halide.

It is indeed known from U.S. Pat. No. 3,102,139, to react, among others, CF$_3$CCl$_3$ in the presence of mercury salts with stabilized SO$_3$. However, the boron oxide named as the stabilizer is as little capable of contributing to the improvement of the reaction as the aluminum trichloride explicitly designated as a usable catalyst. It has therefore not been obvious to carry out experiments with boron halides in the manner according to the invention.

A preferred variant of the process of the invention consists of performing the reaction in the additional presence of only halosulfonic acid. This mode of operation is actually contrary to the teaching of U.S. Pat. No. 3,102,139, according to which the reaction of the fluoroalkane halide/sulfur trioxide/catalyst system must take place in the absence of compounds containing active (Zerewitinoff) hydrogen.

A particularly preferred variant of the process according to the invention resides in carrying out the reaction in the additional presence of boron halide and halosulfonic acid. The best results are obtained with this process variant.

DETAILED DESCRIPTION OF PREFERRED EMBODIMENTS

In all of the cases wherein the reaction takes place in the additional presence of a boron halide, the latter may be added as such to the reaction mixture.

However, it is possible in another variant to produce the boron halide from a suitable boron compound and a halogenating agent in situ.

Suitable boron compounds are those which under the specified reaction conditions together with the halogenating agent, form a boron halide. Particularly suitable boron compounds are oxygen containing boron compounds, such as, for example, boric acid, boron oxide or sodium borate, with sodium tetraborate being especially suitable.

Suitable halogenating agents are those which under the specified reaction conditions yield a boron halide with the boron compound. According to present knowledge, aluminum trichloride is not effective as a halogenating agent. Sulfur halides, sulfur oxyhalides, phosphorus halides, phosphorus oxyhalides and/or halosulfonic acids may be used. The latter are especially preferred, in particular, because in the particularly preferred variant of the process according to the invention the reaction takes place in the presence of both a boron halide and a halosulfonic acid. If, therefore, for the purpose of the in situ formation of the boron halide as the halogenating agent, a stoichiometric excess—with respect to the boron compound to be halogenated—of a halosulfonic acid is used, the particularly preferred process variant is automatically attained.

In all of the cases, wherein the reaction takes place in the additional presence of a halosulfonic acid, it may be added to the reaction mixture as such. However, it is also possible to produce the halosulfonic acid in the reaction mixture in situ, in a manner known in itself. The reaction of SO$_3$ with hydrogen halide is particularly suitable for the in situ production of halosulfonic acid.

The reaction of trifluoro-trichloroethane with SO$_3$ to yield trifluoracetyl chloride—according to the process of the invention—may be carried out at atmospheric pressure in a temperature range of 0° to 120° C., wherein the preferred temperature range is 20° to 80°. But it is entirely possible to let the reaction take place at temperatures over 120° C. and/or at pressures higher than atmospheric, but this requires an additional technical expense.

The process may be effected in batches, semicontinuously or continuously. In a batch-wise operation, the boron halide and/or the halosulfonic acid or the starting compounds used to form this compound or these compounds, may be added subsequently to the reaction mixture present in the reaction vessel ($CF_3CCl_3 + SO_3 +$ mercury salt). The sequence of the additions does not play an essential role, so that it can also be altered. The reaction rate decreases in the course of the reaction as the result of the consumption of the starting components. To obtain a quantitative conversion of the $CF_3CCl_3$, the $SO_3$ is used in excess, whereby favorable space-time yields are obtained when 1 to 10 moles, preferably 1 to 5 moles, of $SO_3$ are available per mole of $CF_3$-$CCl_3$. A $SO_3$ content higher than this in the reaction mixture has no significant effect on the rate and the yield of the reaction.

An effect of the amount of boron halide and/or halosulfonic acid—with respect to the yield and the rate of the reaction—on the reaction may be found to a limited extent. The progress of the reaction is favorable with a boron content of 1 to 30 mole %, preferably 1 to 10 mole %, with respect to the fluorochloroalkane employed. The amounts of the halosulfonic acid are preferably 3 to 140 mole %, in particular 3 to 50 mole %, with respect to the fluorochloroalkane employed. Higher boron halide and/or halosulfonic acid contents increase the reaction rate only slightly.

The trifluoroacetyl chloride formed in the reaction is either obtained directly in a quantitative manner, or it is converted to other trifluoroacetyl compounds in a manner known in itself. Thus, it can be conducted, for example, into ethanol and converted into trifluoroacetic acid ethylester. In place of ethanol, other aliphatic or aromatic alcohols can also be used. Reactions with other compounds which are known to react with acid chlorides are also possible, such as for example, ammonia, amines, water, ketenes, etc. In this manner, valuable trifluoroacetyl compounds are obtained, which may be used in numerous technical fields, for example, in pharmacology and the protection of plants.

EXAMPLES

The trifluoroacetyl chloride yields in mole % with respect to trifluortrichlorethane, obtained in Examples 1 to 7, are presented in Table 1 as a function of reaction time.

EXAMPLE 1

In a 250 ml, three-necked glass flask with a reflux condenser thermostated to 0° C., 1 g $HgSO_4$ and 1 g $H_2SO_4$ are placed. To this mixture, a solution of 93.7 g (0.5 mole) $CF_3$-$CCl_3$ and 162 g (2.0) $SO_3$ is added. Following a further addition of 17.5 g (0.18 mole) $HSO_3F$ the reaction mixture is agitated at room temperature and 2 g $BF_3$ (0.03 mole) are introduced into the solution. Subsequently, the contents of the flask are heated, after which beginning at 30° C. a vigorous development of $CF_3$-COCl is observed. The trifluoroacetyl chloride flows through the reflux condenser, passes through a $H_2SO_4$ scrubber to separate the $SO_3$ entrained and is condensed out in two subsequent cold traps at $-78°$ C. In the course of the reaction, the temperature in the flask rises from 30° to 59° C.

EXAMPLE 2

Into the experimental apparatus described in Example 1, 93.7 g $CF_3CCl_3$ are placed and 2 g $HgSO_4$ are added. The slurry is agitated at 20° C. Subsequently, a solution of 162.0 g $SO_3$, 17.5 g $HSO_3F$ and 2 g $BF_3$ are added in drops. An intensive reaction begins at 38° C. The end temperature in the reaction vessel amounted to 56° C.

EXAMPLE 3

Into the flask of the experimental apparatus described in Example 1, 4 g $H_3BO_3$ and 2 g $HgSO_4$ are weighed. To this, by means of a dropping funnel, a mixture of 93.7 g $CF_3CCl_3$, 162 g $SO_3$ and 17.5 g $HSO_3Cl$ is added. The reaction mixture heats up to 35° C. with a vigorous development of gas.

EXAMPLE 4

Into the experimental apparatus described in Example 1, 11 g $HgSO_4$, 1 g $B_2O_3$ and 93.7 g $CF_3CCl_3$ are added. From a dropping funnel, a solution of 162 g $SO_3$, 20 g $HSO_3Cl$ and 1 g $BF_3$ is added. The temperature in the reaction vessel rises to 37° C.

EXAMPLE 5

Into the experimental apparatus described in Example 1, 2 g $HgSO_4$ and 10 g $BBr_3$ are added. A solution of 93.7 g $CF_3CCl_3$, 162 g $SO_3$ and 4 g $H_2SO_4$ are added in drops. The trifluoroacetylchloride leaving the reflux condenser is passed through a wash flask with $H_2SO_4$ and subsequently fed into a reaction vessel with ethanol. In the process, trifluoroacetic acid ethylester is formed.

EXAMPLE 6

Into the experimental apparatus described in Example 1, a mixture of 1 g $HgSO_4$, 1 g $Hg_2SO_4$, 93.7 g $CF_3CCl_3$, 162 g $SO_3$ and 17.5 g $HSO_3Cl$ is placed. Subsequently, under agitation the reaction mixture is heated to 38° C. In the course of the reaction, the reaction temperature rises to 67° C. After 12 h, the evolution of gas ceases.

EXAMPLE 7

Into the flask of the experimental apparatus described in Example 1, 5 g $Na_2B_4O_7 \times 10\ H_2O$ and 4 g $HgSO_4$ are weighed. From a dropping funnel, a mixture of 94.7 g $CH_3CCl_3$, 162 g $SO_3$ and 20 g $HSO_3Cl$ is added, leading to a vigorous evolution of gas, while the mixture is heating up. The temperature, initially established at 32° C. in the flask, rises after heating for 6 h to 74° C. at the reflux.

EXAMPLE 8

(not according to the invention)

Into the experimental apparatus described in Example 1, a mixture of 94.7 g $CF_3CCl_3$, 162 g $SO_3$, 5 g finely powdered, anhydrous aluminum chloride and 2 g $HgSO_4$ is heated over a period of 4 h. A constant temperature of 38° C. is established in the flask with a good reflux. No gas is evolved and no trifluoroacetyl chloride is obtained.

TABLE I

| | TRIFLUORACETYL CHLORIDE YIELD | | | | | | | | | | | | | |
|---|---|---|---|---|---|---|---|---|---|---|---|---|---|---|
| Reaction | YIELD | | | | | | | | | | | | | |
| Time | Example 1 | | Example 2 | | Example 3 | | Example 4 | | Example 5 | | Example 6 | | Example 7 | |
| [h] | g | % | g | % | g | % | g | % | g | % | g | % | g | % |
| 1 | 16.8 | 25.0 | 37.1 | 55.4 | 35.0 | 52.2 | 35.0 | 52.2 | | | | | | |
| 2 | 34.4 | 52.9 | 42.5 | 63.4 | 47.6 | 71.1 | 47.3 | 70.6 | | | | | 50.2 | 74.9 |
| 3 | 39.1 | 58.4 | 44.9 | 67.0 | 53.7 | 80.2 | 53.4 | 79.7 | | | | | | |
| 4 | 42.3 | 63.2 | 47.0 | 70.1 | 58.1 | 86.7 | 55.9 | 83.4 | | | | | 63.1 | 94.2 |
| 6 | 46.0 | 68.7 | 50.3 | 75.0 | 59.6 | 89.0 | 58.0 | 86.6 | | | | | 63.9 | 95.4 |
| 8 | 47.6 | 71.1 | 53.5 | 79.8 | 60.2 | 89.9 | | | | | | | | |
| 12 | | | | | | | | | 115.8 | 81.0 | 52.3 | 78.0 | | |

We claim:

1. Process for the preparation of trifluoroacetyl chloride ($CF_3COCl$), which comprises the step of reacting 1,1,1-trifluoro-2,2,2-trichloroethane ($CF_3CCl_3$) with sulfur trioxide in the presence of a mercury salt and in the presence of a boron halide $BX_3$ (X=F, Cl, Br, I) and a halosulfonic acid $HSO_3Y$ (Y=F, Cl, Br, I).

2. Process according to claim 1, wherein the boron halide is added to the reaction mixture as such.

3. Process according to claim 1, wherein the boron halide is produced in situ from a boron compound and a halogenating agent.

4. Process according to claim 3, wherein boric acid, boron trioxide and/or sodium borate is used as the boron compound.

5. Process according to claim 4, wherein said boron compound comprises sodium tetraborate.

6. Process according to claim 3 or 4, wherein a compound of the group comprising sulfur halide, sulfur oxyhalide, phosphorus halide, phosphorus oxyhalide, halosulfonic acid and/or a mixture of these, is used as the halogenating agent.

7. Process according to claim 6, wherein halosulfonic acid is used.

8. Process according to claim 1, wherein the quantity of the boron halide or boron compound amounts to 1 to 30 mole% boron with respect to the quantity of trifluorotrichloroethane employed.

9. Process according to claim 8, wherein the quantity of the borom halide or boron compounds amounts to 1 to 10 mole % boron with respect to the quantity of trifluorotrichloroethane employed.

10. Process according to claim 1, wherein the halosulfonic acid is added as such to the reaction mixture.

11. Process according to claim 1, wherein the quantity of halosulfonic acid used amounts to 3 to 140 mole % with respect to the quantity of trifluorotrichloroethane employed.

12. Process according to claim 11, wherein the quantity of the halosulfonic acid used amounts to 3 to 50 mole % with respect to the quantity of trifluorotrichloroethane employed.

13. Process according to claim 1, wherein the quantity of $SO_3$ used is between 1 and 10 mole per mole of the trifluorotrichloroethane employed.

14. Process according to claim 13, wherein the quantity of $SO_3$ used is between 1 and 5 mole of the trifluorotrichloroethane employed.

15. Process according to claim 1, wherein the reaction temperature at atmospheric pressure is between 0° and 120° C.

16. Process according to claim 15, wherein the reaction temperature at atmospheric pressure is between 20° and 80° C.

* * * * *